United States Patent [19]

Goegelman et al.

[11] 4,000,161
[45] Dec. 28, 1976

[54] PROCESS FOR PURIFYING THIENAMYCIN

[75] Inventors: Robert T. Goegelman, Linden; Frederick M. Kahan, Rahway, both of N.J.

[73] Assignee: Merck & Co., Inc., Rahway, N.J.

[22] Filed: Sept. 18, 1975

[21] Appl. No.: 613,822

Related U.S. Application Data

[63] Continuation-in-part of Ser. No. 534,382, Dec. 19, 1974, abandoned.

[52] U.S. Cl. .......................... 260/326.31; 424/274
[51] Int. Cl.² ........................................ C07D 487/04
[58] Field of Search ............................. 260/326.31

[56] References Cited
UNITED STATES PATENTS 3,950,357  4/1976  Kahan et al. ............... 260/326.31

Primary Examiner—Nicholas S. Rizzo
Assistant Examiner—Mary C. Vaughn
Attorney, Agent, or Firm—Richard A. Thompson; Walter Patton; Julian S. Levitt

[57] ABSTRACT

Fermentation broths or impure solutions containing thienamycin, a substance having antibiotic activity against gram-negative and gram-positive microorganisms, are purified using ion exchange resins, polyacrylamide gels or adsorbents such as polyester polymers or polystyrene, hydrophobic crosslinked divinyl benzene polymers.

15 Claims, 1 Drawing Figure

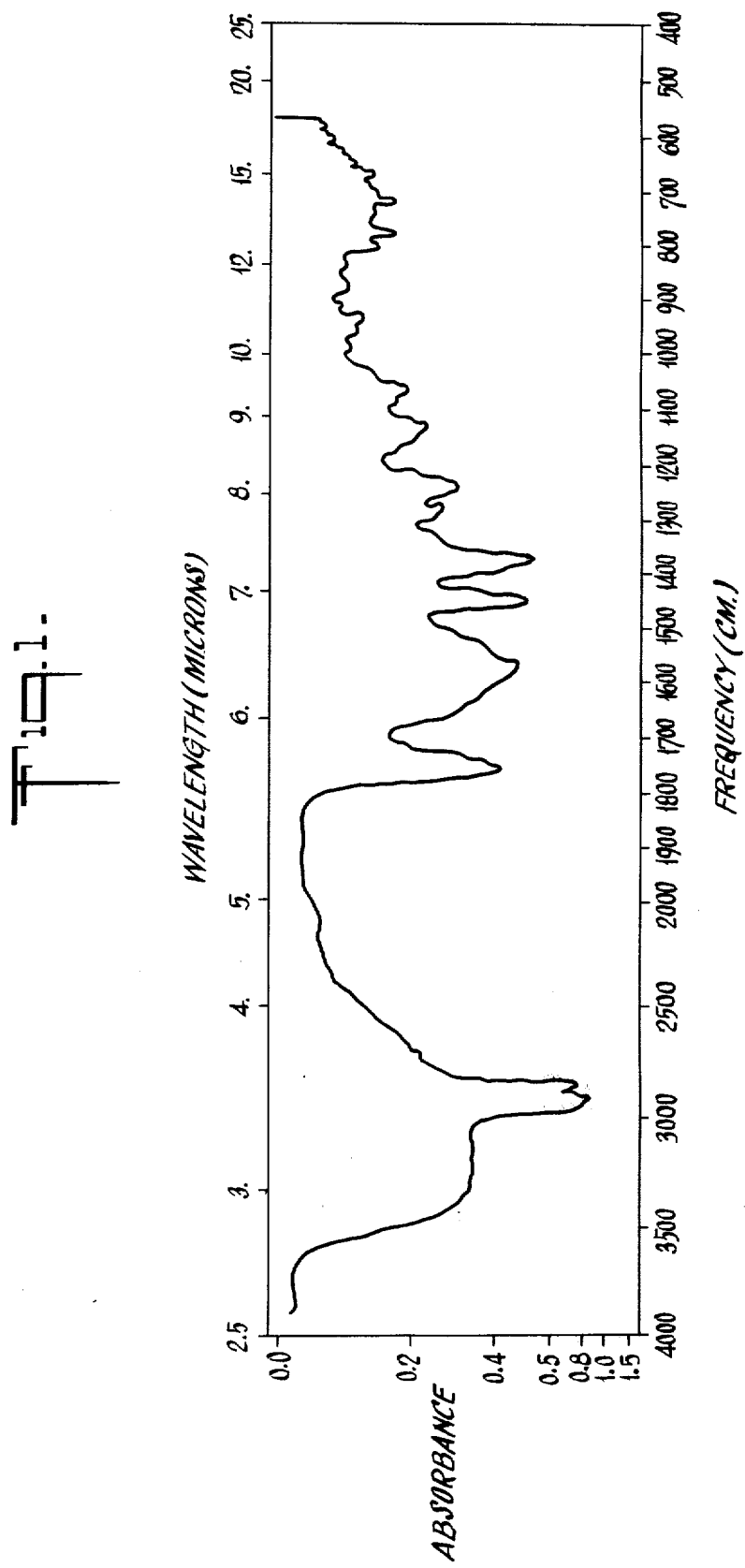

PROCESS FOR PURIFYING THIENAMYCIN

BACKGROUND OF THE INVENTION

This application is a continuation-in-part of our copending application Ser. No. 534,382, filed Dec. 19, 1974, now abandoned.

The antibiotic, thienamycin, is obtained by growing strains of a particular microorganism in suitable aqueous nutrient media under controlled conditions. The present invention is directed to the methods for recovering such an antibiotic in substantially pure, stable form.

SUMMARY OF THE INVENTION

This invention relates to methods for recovering and purifying the novel antibiotic compound, thienamycin, having the following structural formula:

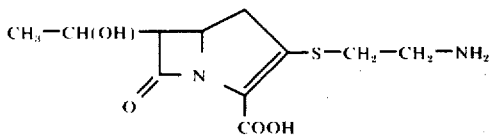

from fermentation broths in which the antibiotic is produced or from solutions containing partially purified antibiotic. This is achieved by contacting the fermentation broth in which the antibiotic is produced or a solution of partially purified antibiotic with an anion or cation exchange resin to absorb the antibiotic on such resin, and thereafter eluting the antibiotic from the resin adsorbate with water or a base, the preferred eluant depending on the type of resin used. The antibiotic of Formula I may also be purified by gel filtration through a poly-acrylamide gel or by chromatography on an adsorbant such as polyester polymers or polystyrene, hydrophobic crosslinked divinyl benzene polymers.

Thienamycin is effective in inhibiting the growth of various gram-negative and gram-positive microorganisms.

DESCRIPTION OF THE PREFERRED EMBODIMENTS

Thienamycin is produced during the aerobic fermentation of suitable aqueous nutrient media, under controlled conditions, by a strain of *Streptomyces cattleya* capable of producing said compound, for instance by the strain on permanent deposit in the culture collection of the Northern Utilization Research and Development Branch of the U.S. Department of Agriculture at Peoria, Ill. under accession number NRRL 8057.

Aqueous media, such as those employed for the production of other antibiotics are suitable for producing thienamycin. Such media contain sources of carbon, nitrogen and inorganic salts assimilable by the microorganism. In general, carbohydrates such as sugars, for example, glucose, fructose, maltose, sucrose, xylose, mannitol and the like and starches such as grains, for example, oats, rye, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1 and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2 to 6% by weight of the aqueous medium.

Among the nutrient inorganic salts which can be incorporated in the culture media are the customary salts capable of yielding sodium, potassium, ammonium, calcium, phosphate, sulfate, chloride, carbonate and like ions. Also included are trace metals such as cobalt, manganese, iron and magnesium.

It should be noted that the media described in the Examples are merely illustrative of the wide variety of media which may be employed, and are not intended to be limitative.

The fermentation is carried out at temperatures ranging from about 20° to 37° C.; however, for optimum results it is preferable to conduct the fermentation at temperatures of from about 22° to 30° C. The pH of the nutrient media suitable for growing the *Streptomyces cattleya* culture and producing thienamycin can vary from about 6.0 to 8.0.

Although the antibiotic thienamycin is produced by both surface and submerged cultures, is is preferred to carry out the fermentation in the submerged state.

It is to be understood that the production of antibiotic is not limited to the organism *Streptomyces cattleya*. In fact, it is desired and intended to include the use of mutants produced from the described organism by various means, such as X-radiation, ultraviolet radiation, nitrogen mustard, phage exposure and the like and also any other thienamycin producing microorganism.

Thienamycin is a valuable antibiotic active against various gram-positive and gram-negative bacteria and, accordingly, finds utility in human and veterinary medicine. The compound can be used as an antibacterial drug for treating infections caused by gram-positive or gram-negative bacteria, for example against *Staphylococcus aureus*, *Proteus mirabilis*, *Escherichia coli*, *Klebsiella pneumoniae*, *Pseudomonas aeruginosa* and *Enterobacter cloacae*. The antibacterial material of the invention may further be utilized as an additive to animal feedingstuffs, for preserving foodstuffs and as disinfectants. For example, it may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of deleterious bacteria.

Tablets and capsules for oral administration may be in unit dose presentation form, and may contain conventional carriers. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives. Suppositories may contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively the active ingredient may be in powder form for reconstitution with a suitable vehicle, e.g. sterile, pyrogen-free water, before use.

Also, in addition to a carrier, the instant compositions may include other ingredients such as stabilizers, binders, antioxidants, lubricators, suspending agents, viscosity agents or flavoring agents and the like.

In veterinary medicine, such as in the treatment of chickens, cows, sheep, pigs and the like, the composition may, for example, be formulated as an intramammary preparation in either long acting or quick-release bases.

In the treatment of bacteria infections in man, the compound of this invention is administered orally or parenterally, in accordance with conventional procedures for antibiotic administration, in an amount of from about 2 to 600 mg./kg/day and preferably about 5 to 100 mg./kg./day in preferably divided dosage, e.g. three to four times a day. They may be administered in dosage units containing, for example, 25, 250, 500 or 1000 mg. of active ingredient with suitable physiologically acceptable carriers or excipients. The dosage units are in the form of liquid preparations such as solutions or suspensions or as solids in tablets or capsules.

The dosage to be administered depends to a large extent upon the condition of the subject being treated, the weight of the host and the type of infection, the route and frequency of administration, the parenteral route being preferred for generalized infections and the oral route for intestinal infections. It will, of course, be understood that smaller doses will be employed for pediatric use, all of such adjustments being within the skill of the practitioner in the field.

The antibiotic containing fermentation broths produced in accordance with the procedures described herein have activities ranging from about 50 to 400 units per ml. when assayed in accordance with the disc-diffusion assay using *Staphylococcus aurreus* ATCC 6538P. Antibiotic preparations having at least 2 units of activity per mg. of broth solids, can be purified and the antibiotic recovered by a number of processes.

One such procedure comprises adsorbing thienamycin on a strongly acidic cation exchange resin at acidic pH and eluting with aqueous organic bases. The eluate so obtained can be further purified by the following processes: chromatography on an anion exchange resin of the polystyrene-quarternary ammonium type; chromatography on a cation exchange resin with a buffer or water; gel filtration and chromatography on an adsorbing resin.

The sequence in which the processes are carried out is not critical, however, it is preferred to use the sequence wherein the ion exchange resin purification is used for the more impure broths and solutions and the gel and polymeric adsorbing resin methods used for material which has already been at least partially purified. Examples of preferred sequences of steps for recovering the antibiotic thienamycin from fermentation broths or from solutions containing the antibiotic comprises passing a fermentation broth or a solution containing the antibiotic through a column packed with a cation exchange resin containing sulfonic acid exchange groups; eluting the resin adsorbate with a base; collecting the eluates; combining the active fractions; and passing the combined fractions through a column packed with polyacrylamide or dextran gel which excludes molecules having a molecular weight greater than 1,800 and 700 respectively; eluting the gel with water or with an aqueous solution of a lower alcohol; collecting the eluates and combining the active fractions.

A further preferred sequence of steps for recovering the antibiotic thienamycin from fermentaton broths or from solutions containing the antibiotic comprises passing a fermentation broth or a solution containing the antibiotic through a column packed with a cation exchange resin containing sulfonic acid exchange groups; eluting the resin adsorbate with a base; collecting the eluates; combining the active fractions; percolating the active fractions eluted from the cation exchange resin through a column packed with an anion exchange resin of the polystyrene-quarternary ammonium type; collecting the effluent; passing the effluent through a column packed with polyacrylamide or dextran gel which excludes molecules having a molecular weight greater than 1,800 and 700 respectively; eluting the gel with water or with an aqueous solution of a lower alcohol; collecting the eluates and combining the active fractions.

A further preferred sequence of steps for recovering the antibiotic thienamycin from fermentation broths or from solutions containing the antibiotic comprises passing a fermentation broth or a solution containing the antibiotic through a column packed with a cation exchange resin containing sulfonic acid exchange groups; eluting the resin adsorbate with a base; collecting the eluates; combining the active fractions; percolating the active fractions eluted from the cation exchange resin through a column packed with an anion exchange resin of the polystyrene-quaternary ammonium type; concentrating the effluent; adsorbing the concentrated effluent on a column packed with a polystyrene, hydrophobic crosslinked divinylbenzene polymer; eluting the polymer with water or a phosphate buffer; collecting the eluate and combining the active fractions, and, in the case of phosphate buffer eluate, repeating the last step of adsorption and elution from the divinylbenzene polymer using water as the eluate.

The present invention is intended thienamycin include the process of adsorbing solutions containing the antibiotic thineamycin and inorganic ions, such as buffer salts, on a column packed with the polystyrene resin, XAD-2, and eluting with water to obtain thienamycin free of inorganic ions.

A still preferred sequence of steps for recovering the antibiotic thienamycin from fermentation broths or from solutions containing the antibiotic comprises passing a fermentation broth or a solution containing said antibiotic through a column packed with a cation exchange resin containing sulfonic acid exchange groups; eluting the resin adsorbate with a base; collecting the eluates; combining the active fractions; percolating the active fractions eluted from the cation exchange resin through a column packed with an anion exchange resin of the polystyrene-quarternary ammonium type; collecting the effluent; passing the effluent through a column packed with a cation exchange resin containing nuclear sulfonic acid exchange groups; eluting the resin adsorbate with a buffer or water; combining the active fractions; passing the active fractions through a column packed with polyacrylamide or dextran gel which excludes molecules having a molecular weight greater than 1,800 and 700 respectively; eluting the gel with water or dilute buffer or with an aqueous solution of a lower alcohol; collecting the eluates combining the active fractions, concentrating said fractions, adsorbing them on a column packed with the polystyrene resin, XAD-2, and eluting with water.

Examples of useful sequences of purification steps which may be employed are:

1. Chromatography on a cation exchange resin; chromatography on an anion exchange resin; a repeated chromatography on a cation exchange resin; adsorption and elution from an adsorbing resin followed by a second adsorption and elution from an adsorbing resin.

2. Chromatography on a cation exchange resin; chromatography on an anion exchange resin; a repeated chromatography on a cation exchange resin; adsorption and elution from an adsorbing agent; gel filtration.

3. Chromatograpy on an anion exchange resin; chromatography on a cation exchange resin; gel filtration; adsorption and elution from an adsorbing resin.

A preferred method of purifying thienamycin comprises adsorbing thienamycin on a strongly acidic cation exchange resin wherein the counter-ion on the resin is selected from any suitable counter-ion presently known in the art such as sodium or potassium. Illustrative of such resins are those of the sulfonate type having a styrene-divinylbenzene matrix, for example the polystyrene nuclear sulfonic acid resin Dowex 50 × 2 (manufactured by Dow Chemical Co., Midland, Mich.), on the sodium cycle. Other representative members of the class of strong cation exchange resins include the following: Dowex 50 × 4, Dowex 50 × 8 (manufactured by Dow Chemical Co., Midland, Mich.), Amberlite IR120 (manufactured by Rohm and Haas Co., Philadelphia, Pa.), Duolite C25D (manufactured by Chemical Process Co., Redwood City, Calif.) Permutit Q (manufactured by Permutit Co., Birmingham, N.J.), Ionac C-249 (manufactured by Ionac Chemical Co., Birmingham, N.J.) and Amberlite 200.

The adsorbed antibiotic is readily eluted from the cation exchange resin with aqueous solution of organic bases such as pyridine; $\alpha$, $\beta$ or $\gamma$ picoline; 2,3-;2,4- and 2,6-lutidine; 2,4,6-collidine and alkyl amines wherein the alkyl groups contain 2 to 10 carbon atoms and wherein the preferred number of carbon atoms is 2 to 6. The preferred base for eluting the cation exchange resin is pyridine. The eluate so obtained can be further purified, if desired, by other purification procedures. Further purification may be achieved, for example, by chromatography on an anion exchange resin of the polystyrene-trimethylammonium type wherein the negative counter-ion is selected from any suitable counter-ion that is presently known in the art, such as chloride or acetate. The eluate so obtained can be further purified by chromatography at a constant pH with a volatile or non-volatile buffer on a cation exchange resin of the polystyrene-sulfonate type.

The buffers which may be used are those which can maintain the pH in the range of 6 to 8. Suitable non-volatile buffers are prepared from tris(hydroxymethyl)aminomethane maleate, cacodylic acid, $KH_2PO_4$ or $NaH_2PO_4$. The preferred non-volatile buffer is $NaH_2PO_4$. Suitable volatile buffers are prepared from N-ethylmorpholine, $\alpha$-, $\beta$- or $\gamma$- picolines, or 2,3-;2,4- or 2,6-lutidine. The preferred volatile buffer is 2,6-lutidine.

The eluate obtained from the cation exchange resin chromatography is passed through a gel filtration resin such as a polyacrylamide or destran gel. Generally, a gel of 50-100 mesh which will allow the fractionation and desalting of substances with molecular weights from 200-2000 is used. Gels of 50-400 mesh may also be employed, the particular mesh employed depending upon the size of the column to be used. Examples of suitable gels are dextran cross-linked with equichlorhydrin and available in bead form as Sephadex G-10 from the Pharmacia Company, Sweden which excludes molecules having a molecular weight greater than 700, and polyacrylamides cross-linked with methylene bisacrylamide available in bead form as Bio-Gel P-2 from Bio Rad Laboratories, Richmond, Calif. which excludes molecules having a molecular weight greater than 1800. The pH of the antibiotic solution to be purified is preferably adjusted to about neutral, and the solution contacted and equilibrated with the gel. The antibiotic is then removed from the gel with water or another suitable eluting agent such as an aqueous solution of a lower alchohol. The eluate is collected in fractions and those determined to be most active by bioassay are combined.

A specifically preferred method for recovering purified thienamycin is to pass a solution of the antibiotic, such as the filtered fermentation broth, the pH of which has been adjusted between 3 to 5 through a column containing a strong cation exchange resin of the sulfonate type in the sodium cycle (Dowex 50 × 2). The resulting adsorbate is then eluted with a suitable eluant such as 2% aqueous pyridine. The eluates are collected in fractions, the size of the fraction depending upon the size of the column employed. Further purification may be achieved by the following sequence of processes; chromatography on an anion exchange resin of the polystyrene-trimethylammonium type (e.g. Dowex-1 × 2 in the chloride or acetate cycle); chromatography on a cation exchange resin of the polystyrene-sulfonate type (e.g. Dowex-50 in the 2,6-lutidinium cycle) wherein the column is eluted with 2,6-lutidine acetate buffer at pH 6.3; gel filtration through gel-permeation resins (e.g. Bio-Gel P-2, a polyacrylamide resin) and one or more cycles of adsorption on and elution from a polymeric absorbent (e.g. XAD-2, a polystyrene resin) employing dilute phosphate buffers at neutral pH or water. The bioactivity of the eluates is measured by assaying the eluate using *Staphylococcus aureus* ATCC 6538P as the assay organism.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of an identical product should by construed as constituting an analogous method. The described processes are capable of wide variation and any minor departure or extension is considered as being within the skill of the artisan and as falling within the scope of this invention.

ASSAY

Assays of antibacterial activity are run according to the following disc-diffusion procedure unless otherwise indicated. The assay plates are prepared in the following manner. An overnight growth of the assay organism, Staphylococcus aureus ATCC 6538P, in nutrient broth plus 0.2% yeast extract is diluted with nutrient broth plus 0.2% yeast extract to a suspension having 55% transmittance at a wavelength of 660 mμ. This suspension is added to Difco nutrient agar supplemented with 2.0 g./l. Difco yeast extract, at 47° to 48° C., to make a composition containing 33.2 ml. of the suspension per liter of agar. Five ml. aliquots of this suspension is poured into petri dishes of 85 mm. diameter, and these plates are chilled and held at 4° C. until used (5 day maximum).

Samples of the antibiotic to be assayed are diluted to an appropriate concentration in phosphate buffer at pH 7. Filter-paper discs, 0.5-inch in diameter, are dipped into the test solution and placed on the surface of the assay plate; two discs for each sample are normally placed on one plate opposite to one another. The plates are incubated overnight at 37° C. and the zone of inhibition is measured as mm. diameter. The zone of inhibition measured in mm. determines relative potencies or, when compared with a purified reference standard such as cephalothin, the potency of antibiotic in units/ml. The unit of activity reported in Examples 4 through 7 is based on cephalothin standard solutions of 8, 4, 2 and 1 μg./ml. One unit is defined as the amount which calculates to produce the same inhibition as 1 μg. of cephalothin/ml. that zone of inhibition being between 16 and 21 mm. diameter.

EXAMPLE 1

A tube of lyophilized culture of Streptomyces cattleya is opened aseptically and the contents suspended in a tube containing 0.7 ml. of sterile Davis salts having the following composition:

| Davis Salts | | |
|---|---|---|
| Sodium citrate | 0.5 | g |
| $K_2HPO_4$ | 7.0 | g |
| $KH_2PO_4$ | 3.0 | g |
| $(NH_4)_2SO_4$ | 1.0 | g |
| $MgSO_4.7H_2O$ | 0.1 | g |
| Distilled $H_2O$ | 1000 | ml |

A 0.2 ml. portion of this suspension is used to inoculate a culture slant of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| $MgSO_4.7H_2O$ | 0.05 | g |
| Distilled $H_2O$ | 1000 | ml |
| pH: adjust to 6.5 using NaOH | | |
| *Ardamine: Yeast Products Corporation | | |
| +Phosphate Buffer Solution | | |
| $KH_2PO_4$ | 91.0 | g |
| $Na_2HPO_4$ | 95.0 | g |
| Distilled $H_2O$ | 1000 | ml |
| For Slants: add agar - 25.0 g/l | | |

The inoculated slant is incubated for 8 days at 28° C. and then stored at 4° C.

A portion of the spores and aerial mycelia of this slant is used to inoculate a baffled 250 ml. Erlenmeyer seed flask containing 50 ml. of Medium A (without agar). This seed flask is shaken at 28° C. on a 220 rpm shaker (2 inch throw) for two days at which time the growth is satisfactory.

Fifteen 250 ml. Erlenmeyer flasks, each containing 40 ml. of Medium B, are inoculated with 1 ml. per flask of the growth from the seed flask. The Medium B has the following composition:

| Medium B | | |
|---|---|---|
| Corn Meal | 20.0 | g |
| Distiller's Solubles | 10.0 | g |
| Soybean Meal | 15.0 | g |
| Sodium Citrate | 4.0 | g |
| $CaCl_2.2H_2O$ | 0.5 | g |
| $MgSO_4.7H_2O$ | 0.1 | g |
| $CoCl_2.6H_2O$ | 0.01 | g |
| $FeSO_4.7H_2O$ | 0.01 | g |
| **Polyglycol 2000 | 0.25% | by Vol. |
| Distilled $H_2O$ | 1000 | ml |
| pH: adjust to 6.5 using NaOH | | |

**Polyglycol 2000: Dow Chemical Co.

These 15 production flasks are shaken at 28° C. on a 220 rpm shaker (inch inch. throw) for up to 3 days with assays performed during the fermentation cycle. Assays are performed using centrifuged broth. Prior to assay, the pH of the broth is adjusted as shown in the following table.

| Age (Hours) | 48 | 53 | 72 |
|---|---|---|---|
| Activity vs ATCC 6538P (mm. zone) | 34/40h | 35/41h | 34 |
| pH, initial | 6.3 | 5.9 | 5.0 |
| pH, adjusted | — | 6.8 | 6.2 | h = hazy

At 53 hours age, the broths from 13 flasks are pooled. An aliquot is centrifuged and assayed. The remaining broth is filtered, adjusted to pH 7, and 500 ml. is freeze-dried to yield 10.7 g. of solids. A 1.5 g. portion of these solids is taken up in 25 ml. of n-butyl alcohol:water (1:99). The pH of the solution is 7.0. This solution is applied to a 5 × 118 cm. column of Bio-Gel P-2 (200-400 mesh) which has previously been equilibrated with n-butyl alcohol:water. The gel is developed with the same solution at 10 ml./min. collecting a 650 ml. forerun followed by 75 fractions of 20 ml. each. The effluent stream is monitored with a Meccomatic recording differential refractometer. Each fraction is assayed for antibacterial activity. Thienamycin is found in fractions 34 through 40 with a maximum in fraction 37. Ten ml. of fraction 37 are freeze-dried to yield 2.0 mg. of solids. The solids obtained are taken up in 5 ml. of water for assay. Assay plates are incubated overnight at 28° C. The results are tabulated below:

| Concentration | Zone size in mm. vs. Staph. Aureus ATCC 6538P |
|---|---|
| 80 μg./ml. | 30 mm |
| 40 μg./ml. | 25 mm |
| 20 μg./ml. | 21 mm |

-continued

| Concentration | Zone size in mm. vs. Staph. Aureus ATCC 6538P |
|---|---|
| 10 μg./ml. | 17 mm |

EXAMPLE 2

A tube of lyophilized culture of *Streptomyces cattleya* is opened aseptically and the contents suspended in 0.8 ml. of sterile Davis salts having the followig composition:

| Davis Salts | |
|---|---|
| Sodium citrate | 0.5 g |
| $K_2HPO_4$ | 7.0 g |
| $KH_2PO_4$ | 3.0 g |
| $(NH_4)_2SO_4$ | 1.0 g |
| $MgSO_4.7H_2O$ | 0.1 g |
| Distilled $H_2O$ | 1000 ml |

This suspension is used to inoculate 4 slants of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| $MgSO_4.7H_2O$ | 0.05 | g |
| Distilled $H_2O$ | 1000 | ml |
| pH: adjust to 6.5 using NaOH | | |
| *Ardamine: Yeast Products Corporation | | |
| +Phosphate Buffer Solution | | |
| $KH_2PO_4$ | 91.0 | g |
| $Na_2HPO_4$ | 95.0 | g |
| Distilled $H_2O$ | 1000 | ml |
| For Slants: add agar - 25.0 g/l | | |

The inoculated slants are incubated for 1 week at 28° C. and then stored at 4° C.

A portion of the spores and aerial mycelia of one of the slants is used to inoculate a baffled 250 ml. Erlenmeyer seed flask containing 50 ml. of Medium A. This seed flask is shaken at 28° C. on a 220 rpm shaker (2 inch throw) for two days at which time the growth is satisfactory.

Fifteen 250 ml. Erlenmeyer flasks, each containing 40 ml. of Medium B, are inoculated with 1 ml. per flask of the growth from the seed flask. The Medium B has the following composition:

| Medium B | | |
|---|---|---|
| Corn Meal | 20.0 | g |
| Distiller's Solubles | 10.0 | g |
| Soybean Meal | 15.0 | g |
| Sodium Citrate | 4.0 | g |
| $CaCl_2.2H_2O$ | 0.5 | g |
| $MgSO_4.7H_2O$ | 0.1 | g |
| $CoCl_2.6H_2O$ | 0.01 | g |
| $FeSO_4.7H_2O$ | 0.01 | g |
| **Polyglycol 2000 | 0.25% | by Vol. |
| Distilled $H_2O$ | 1000 | ml |
| pH: adjust to 6.5 using NaOH | | |

**Polyglycol 2000: Dow Chemical Co.

These flasks are shaken at 28° C. on a 220 rpm shaker (2 inch throw) for up to 3 days with assays performed during the fermentation cycle. Assays are performed using the supernatant of centrifuged broth. The results are as follows:

| Age (Hours) | 48 | 53 | 72 | |
|---|---|---|---|---|
| pH | 6.7 | 6.4 | 5.5 | |
| Activity vs ATCC 6538P | 38 | 40 | 38 | mm. |

At 53 hours age, the broths from 13 flasks are pooled and filtered. The pH of a 400 ml. portion of the filtrate is adjusted to 4.8 with dilute HCl, and this is adsorbed on 140 ml. of Dowex 50 × 2 $Na^+$ at the rate of 14 ml./min. The adsorbate is washed with 200 ml. of deionized water and eluted with 2% pyridine in water collecting 6 × 70 ml. fractions. The pH of the fractions is adjusted to 7.0.

Assays are run on all fractions and the zone diameters are tabulated below:

| Filtered Broth | |
|---|---|
| Dilution | Zone Diameter |
| 1:4 | 33 mm |
| 1:8 | 30 mm |
| 1:16 | 27 mm |
| 1:32 | 24 mm |
| Eluate Fractions | | |
|---|---|---|
| Dilution | | Zone Diameter |
| 1. | 1:5 | 22.5 mm |
| 2. | 1:5 | 36 mm |
| 3. | 1:5 | 20 mm |
| 4, 5 & 6 | 1:5 | 0 mm |

These assays indicate that 45% of the acitivity is in the eluates. Eluate fraction No. 2 is freeze-dried to yield 117 mg. of solids.

The 117 mg. of solids are dissolved in 1.5 ml. of n-butyl alcohol:water (1:99). The solution is applied to a bed of Bio-Gel P-2 1.4 × 81.5 cm. which has been previously equilibrated with n-butyl alcohol:water. The gel is developed with n-butyl alcohol:water at 1 ml./min. collecting 2 ml. fractions. The effluent stream is monitored with a Meccomatic recording refractometer. Fractions are assayed for antibacterial activity at a dilution of 1:20. Thienamycin bioactivity is observed in fractions 44 through 53. Fractions 46 through 49 and half of fraction 50 are combined. A one ml. sample of the combined fractions is removed for reassay and the remainder freeze-dried to yield 4.2 mg. of partially purified antibiotic.

EXAMPLE 3

A tube of lyophilized culture *Streptomyces cattleya* is opened aseptically and the contents suspended in 0.8 ml. of sterile Davis salts having the following composition:

| Davis Salts | |
|---|---|
| Sodium citrate | 0.5 g |
| $K_2HPO_4$ | 7.0 g |
| $KH_2PO_4$ | 3.0 g |
| $(NH_4)_2SO_4$ | 1.0 g |
| $MgSO_4.7H_2O$ | 0.1 g |
| Distilled $H_2O$ | 1000 ml |

This suspension is used to inoculate four slants of Medium A (plus agar) having the following composition:

| Medium A | | |
|---|---|---|
| Yeast Autolysate (Ardamine*) | 10.0 | g |
| Glucose | 10.0 | g |
| †Phosphate Buffer | 2.0 | ml |
| $MgSO_4.7H_2O$ | 0.05 | g |
| Distilled $H_2O$ | 1000 | ml |
| pH: adjust to 6.5 using NaOH | | |
| *Ardamine: Yeast Products Corporation | | |
| †Phosphate Buffer Solution | | |
| $KH_2PO_4$ | 91.0 | g |
| $Na_2HPO_4$ | 95.0 | g |
| Distilled $H_2O$ | 1000 | ml |
| For Slants: add agar - 25.0 g/l | | |

The inoculated slants are incubated for one week at 28° C. and stored at 4° C. A portion of the spores and aerial mycelia of one of the slants is used to inoculate three baffled 250 Erlenmeyer seed flasks, each containing 50 ml. of Medium A. These seed flasks are shaken at 28° C. on a 220 rpm shaker (2 inch throw) for one day at which time the growth is satisfactory.

Twelve 2000 ml. Erlenmeyer flasks, each containing 250 ml. of Medium C, are each inoculated with 7 ml. of suspension is obtained by the aseptic pooling of the contents of the 3 seed flasks. The Medium C has the following composition:

| Medium C | | |
|---|---|---|
| Corn Meal | 20.0 | g |
| Distiller's Solubles | 10.0 | g |
| Soybean Meal | 15.0 | g |
| $CaCl_2.2H_2O$ | 0.5 | g |
| $MgSO_4.7H_2O$ | 0.1 | g |
| $CoCl_2.6H_2O$ | 0.01 | g |
| $FeSO_4.7H_2O$ | 0.01 | g |
| $CaCO_3$ | 4.0 | g |
| **Polyglycol 2000 | 0.25% | by Vol. |
| Distilled $H_2O$ | 10000 | ml |
| pH: adjust to 6.5 using NaOH | | |

These flasks are shaken at 28° C. on a 220 rpm shaker (2 inch throw) for 72 hours. The broths are pooled, and an aliquot centrifuged for assay. The harvested broth has a pH of 7.4 and the antibacterial assay using the supernatant of centrifuged broth is 43 mm.

The broth is filtered and the pH of the filtrate adjusted to 4.0 with dilute HCl and 3000 ml. is adsorbed on 300 ml. of Dowex 50 × 2 $Na^+$ at the rate of 30 ml./min. The adsorbate is washed with 300 ml. of deionized water and eluted with 2% pyridine collecting 8 × 150 ml. fractions. The pH of the fractions is adjusted to 7.0. Eluate fractions No. 2 and No. 3, comprising 300 ml. are pooled and contain 48% of the total bioactive material applied on the Dowex 50 × 2 $Na^+$ column.

A 280 ml. portion of the pooled fractions of Dowex 50 × 2 $Na^+$ eluate at pH 7.0, obtained above is percolated through a 40 ml. column of Dowex 1 × 2 $Cl^-$ cycle resin. The resin is washed with 160 ml. of deionized water. The effluent and wash fractions are combined to give 440 ml. of solution. This solution is adjusted to pH 8.2 with dilute sodium hydroxide, concentrated under reduced pressure to 300 ml., adjusted to pH 7.0 with dilute HCl and freeze-dried to yield 189 mg. of solids.

The freeze-dried solids, 189 mg., obtained above are dissolved in n-butyl alcohol:water (1:99). The solution, 25 ml., is applied to a column of Bio-Gel P-2 (200-400 mesh), 5 × 108 cm. which has previously been equilibrated with n-butyl alcohol:water. The gel is then developed with n-butyl alcohol:water at 6.7 ml./min. The effluent stream is monitored with a Mecco-matic recording differential refractometer. A five-hundred ml. forerun is taken followed by fractions of 20 ml. each. Every fraction is assayed for antibacterial activity at a dilution of 1.25. The bio-activity is observed in fractions 37 through 42, having a maximum at fraction 39. Fractions 38 through 41, having a total volume of 80 ml., are combined. This solution is concentrated to 10 ml. at pH 7.0 and freeze-dried. The freeze-dried solid, 13.5 mg., has a relative potency approximately sixfold higher than the potency sixfold higher than the potency of the sample charged to the Bio-Gel P-2 column based on comparison by *Staphylococcus aureus* disc-diffusion assays.

EXAMPLE 4

A tube of lyophilized culture of *Streptomyces cattleya* is opened aseptically and the contents suspended in 0.8 ml. of sterile Davis salts having the following compositions

| Davis Salts | | |
|---|---|---|
| Sodium citrate | 0.5 | g |
| $K_2HPO_4$ | 7.0 | g |
| $KH_2PO_4$ | 3.0 | g |
| $(NH_4)_2SO_4$ | 1.0 | g |
| $MgSO_4.7H_2O$ | 0.1 | g |
| Distilled $H_2O$ | 1000 | ml |

This suspension is used to inoculate four slants of Medium A (plus agar) having the following composition:

| Medium Z | | |
|---|---|---|
| Yeast Autolysate (Ardamine*) | 10.0 | g |
| Glucose | 10.0 | g |
| †Phosphate Buffer | 2.0 | ml |
| $MgSO_4.7H_2O$ | 0.05 | g |
| Distilled $H_2O$ | 1000 | ml |
| pH: adjust to 6.5 using NaOH | | |
| *Ardamine: Yeast Products Corporation | | |
| †Phosphate Buffer Solution | | |
| $KH_2PO_4$ | 91.0 | g |
| $Na_2HPO_4$ | 95.0 | g |
| Distilled $H_2O$ | 1000 | ml |
| For Slants: add agar - 25.0 g/l | | |

The inoculated slants are incubated for 1 week at 28° C. and then stored at 4° C.

Ten ml. of Medium A is transferred aseptically to one of these slants, the spores and aerial mycelia scraped into suspension, and 3.3 ml. of this suspension used to inoculate a 2 liter baffled Erlenmeyer flask containing 500 ml. of Medium A. This seed flask is shaken at 28° C. on a 160 rpm shaker (2 throw) for 48 hours at which time the growth is satisfactory.

The growth from this seed flask is used to inoculate a 190 liter stainless steel seed tank containing 160 liters of Medium A. This tank is operated at 28° C. using an agitation rate of 150 rpm and an airflow of 3 cu. ft. per minute for 24 hours. Defoamer, Polyglycol 2000 (Doe Chemical Corp.), is used as required by not to exceed 0.1%. pH determinations are made as follows:

| Age, Hours | 0 | 12 | 24 |
|---|---|---|---|
| pH | 6.4 | 6.4 | 6.3 |

Forty-three liters of the growth in this seed tank is used to inoculate a 756 liter stainless steel fermentor containing 467 liters of Medium E, wherein Medium E has the composition:

| Medium E | | |
|---|---|---|
| Cerelose | 25.0 | g |
| Corn Steep Liquor (wet basis) | 15.0 | g |
| Distiller's Solubles | 10.0 | g |
| Cottonseed Media (Pharmamedia) | 5.0 | g |
| $CoCl_2.6H_2O$ | 0.01 | g |
| $CaCO_3$ (after pH adjustment) | 3.0 | g |
| Polyglycol 2000 | 0.25% | |
| Tap water | 1000 | ml |
| pH: adjust to 7.3 using NaOH | | |

This tank is run at 24° C. using an agitation rate of 95 rpm and an airflow of 10 cu. ft. per minute for 120 hours. Additional defoamer, Polyglycol 2000, is added as required, not to exceed 0.1%. Antibacterial assays are run and the data is as follows:

| Age | pH | Antibiotic Activity vs ATCC 6538P (mm) | Dextrose mg./ml. |
|---|---|---|---|
| 0 | 6.8 | — | 22 |
| 12 | 6.6 | — | 21.3 |
| 24 | 6.2 | — | 16.5 |
| 36 | 5.8 | 25 | 12.1 |
| 48 | 5.7 | 25 | 7.8 |
| 60 | 5.8 | 21.5 | 4.3 |
| 72 | 6.1 | 25 | 2.5 |
| 84 | 6.6 | 33 | 1.6 |
| 96 | 6.7 | 41.5 | 1.0 |
| 108 | 6.5 | 45 | 1.0 |
| 120 | 6.5 | 45 | 0.5 |

Four-hundred liters of whole broth is filtered using a filter press and filter aid admix. 1.2 G. of (ethylenedinitrilo) tetraacetic acid, sodium salt is added to the filtrate. The filtrate is cooled to 6° C., adjusted to pH 4.0 ± 0.2 and maintained at 6° C. The cold filtrate is adsorbed on 38 liters of Dowex 50 × 4 $Na^+$, 20–50 mesh at 4 liters/minute. The adsorbate is washed with 40 liters of deionized water. The adsorbate is eluted with 2% aqueous pyridine and three fractions of 19 liters each are collected and assayed. The antibacterial assay indicates that eluate fractions 2 and 3 contain 22% of the applied activity. These fractions are combined, concentrated to 3.8 liters and adjusted to pH 7.

The 3.8 liters concentrate obtained above is adsorbed on 2.5 liters of Dowex 1 × 2, 50 to 100 mesh, chloride cycle resin at 200 ml./min. The resin is eluted with deionized water at the same rate. Ten 1 liter fractions are collected and each fraction adjusted to pH 7.0 as required. Assays indicated 75% of the bio-activity is in fractions 5 through 8. These fractions are combined and filtered using a 0.45 micron Millipore. A 3 liter portion of this filtrate is freeze-dried to yield 16.6 grams of solids having a potency of 70 units/mg.

Four grams of freeze-dried solids obtained above are taken up in 50 ml. of 0.1M 2,6-lutidine acetate buffer, pH 6.3. The solution is restored to pH 6.3 by addition of acetic acid, and applied to a Dowex 50 × 8 column prepared as follows:

A 2.5 liter amount of Dowex 50 × 8 (20–400 mesh) hydrogen cycle resin is converted to the 2,6-lutidine cycle. The resin is equilibrated with five column volumes of 0.1M 2,6-lutidine acetate, pH 6.3, buffer. The dimensions of the equilibrated resin bed are 5 × 114 cm. The column is developed with 0.1M buffer at 14 ml./min.

The effluent stream is monitored with a Meccomatic recording differential refractometer. The development is carried out until 220 fractions, 20 ml. each, are collected. Every other fraction from 44 through 142 is assayed at a dilution of 1:50. The bio-activity is observed in fractions 78 through 136, reaching a maximum in fractions 92 through 94. Fractions 82 through 116 are selected and combined to yield 700 ml. of solution. This solution is divided into two 350 ml. portions and freeze-dried.

One portion of the freeze-dried solids is dissolved in 0.1M 2,6-lutidine acetate, pH 7.0 buffer. The solution, 27 ml., is applied to a column of Bio-Gel P-2 (200–400 mesh) 5 × 108 cm. which has previously been equilibrated with 0.1M buffer. The gel is then developed with the same buffer at 10 ml./min.

The effluent stream is monitored with a Meccomatic recording differential refractometer. The development is continued until 105 fractions, 20 ml. each, are collected. Every fraction from 51 through 90 is assayed at a 1:50 dilution. The assay reveals a bio-active peak in fractions 67 through 75, with a maximum in fractions 70 and 71. Fractions 68 through 75 L are combined to yield a volume of 162 ml. To 145 ml. of the combined fraction, 3 ml. of 360 mM. pH 7.0 sodium phosphate buffer is added and the solution is concentrated to 9 ml. The concentrate, which contains 78% of the total bio-active material applied on the Bio-Gel P-2 column, is freeze-dried to yield 185 mg. A remaining 17 ml. aliquot of fractions 68 through 75 is freeze-dried to yield 1.9 mg. of solids which has a potency of 1050 units/mg.

EXAMPLE 5

A tube of lyophilized culture of *Streptomyces cattleya* is opened aseptically and the contents suspended in 0.88 ml. of sterile Davis salts having the following composition:

| Davis Salts | | |
|---|---|---|
| Sodium citrate | 0.5 | g |
| $K_2HPO_4$ | 7.0 | g |
| $KH_2PO_4$ | 3.0 | g |
| $(NH_4)_2SO_4$ | 1.0 | g |
| $MgSO_4.7H_2O$ | 0.1 | g |
| Distilled $H_2O$ | 1000 | ml. |

This suspension is used to inoculate four slants of Medium A (plus agar) having the following composition:

| Medium A | | |
|---|---|---|
| Yeast Autolysate (Ardamine*) | 10.0 | g |
| Glucose | 10.0 | g |
| +Phosphate Buffer | 2.0 | ml |
| $MgSO_4.7H_2O$ | 0.05 | g |
| Distilled $H_2O$ | 1000 | ml |
| pH: adjust to 6.5 using NaOH | | |
| *Ardamine: Yeast Products Corporation | | |
| +Phosphate Buffer Solution | | |
| $KH_2PO_4$ | 91.0 | g |
| $Na_2HPO_4$ | 95.0 | g |

-continued

| Medium A | | |
|---|---|---|
| Distilled H₂O | 1000 | ml |
| For Slants: add agar - 25.0 g/l | | |

The inoculated slants are incubated for 1 week at 28° C. and then stored at 4° C.

Ten ml. of Medium A is transferred aseptically to one of these slants, the spores and aerial mycelia are scraped into suspension, and 3.3 ml. of this suspension is used to inoculate a 2 L. liter baffled Erlenmeyer flask containing 500 ml. of Medium A. This seed flask is shaken at 28° C. on a 160 rpm (2 throw) for 48 hours.

The growth from this seed flask is used to inoculate a 190 liter stainless steel seed tank containing 160 liters of Medium A. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1 %. pH determinations are made as follows:

| Age, Hours | 0 | 12 | 24 |
|---|---|---|---|
| pH | 6.3 | 6.6 | 5.6 |

Thirty-five liters of the growth in this seed tank is used to inoculate a 756 liter stainless steel fermentor containing 467 liters of Medium E, wherein Medium E has the composition:

| Medium E | | |
|---|---|---|
| Cerelose | 25.0 | g |
| Corn Steep Liquor (wet basis) | 15.0 | g |
| Distiller's Solubles | 10.0 | g |
| Cottonseed Media (Pharmamedia) | 5.0 | g |
| CoCl₂.6H₂O | 0.01 | g |
| CaCO₃ (after pH adjustment) | 3.0 | g |
| Polyglycol 2000 | 0.25% | |
| Tap water | 1000 | ml |
| pH: adjust to 7.3 using NaOH | | |

This tank is operated at 24° C. using an agitation rate of 95 rpm and an airflow of 10 cu. ft. per minute for 120 hours. Defoamer, Polyglycol 2000, is added as required, but not to exceed 0.1%. Antibacterial assays are performed and the data is as follows:

| Age | pH | Antibiotic Activity vs ATCC 6538P |
|---|---|---|
| 0 | 6.9 | — |
| 12 | 6.8 | — |
| 24 | 6.3 | — |
| 36 | 6.4 | 26 |
| 48 | 6.3 | 32 |
| 60 | 6.4 | 25 |
| 72 | 6.8 | 25 |
| 84 | 7.0 | 25 |
| 96 | 7.1 | 37 |
| 108 | 7.2 | 41.5 |
| 120 | 7.1 | 44.5 |

Four-hundred liters of the whole broth is filtered using a filter press and filter aid admix to the extent of 4% w/v. 1.2 G. of (ethylenedinitrilo) tetraacetic acid, sodium salt is added to the filtrate. The filtrate is cooled to 6° C., adjusted to pH 4.0 ± 0.2 and maintained at 6° C. The cold filtrate is adsorbed on 38 liters of Dowex 50 × 4 Na⁺, 20–50 mesh as 4 liters/minute. The adsorbate is eluted with 2% aqueous pyridine and three fractions of 19 liters each are collected and assayed. The assay indicated 27% of input bioactivity is in fractions 2 and 3. Eluate fractions 2 and 3 are combined, concentrated to 3.7 liters and adjusted to pH 7.

The eluate concentrate of 3.7 liters is adjusted to pH 7.4 and adsorbed on 2.5 liters of Dowex 1 × 2 Cl⁻ cycle resin (50–100 mesh) at 200 ml./min. The resin is then eluted with deionized water at the same rate. Two × 2 liters; 1 × 800 ml; 1 × 4 liters and 1 × 2 liter fractions are collected, adjusting pH to 7.0 as required. Fraction 4 (4 liters), which contains 50% of the activity present in the concentrate, is filtered using a Millipore 0.45 micron filter. The clear filtrate is tray freeze-dried to yield 12.4 grams of solids which had a potency of 270 units/mg.

Four grams of the freeze-dried solids is taken up in 0.1M 2,6-lutidine acetate buffer, pH 6.3. The solution, 50 ml., restored to pH 6.3 by addition of acetic acid, is applied to a column of Dowex 50 × 8; 2,6-lutidine cycle resin (200–400 mesh) having the dimensions 5 × 114 cm. which had previously been equilibrated with 0.1M buffer. The resin is then developed with the same 0.1M pH 6.3 buffer at 14 ml./min.

The effluent stream is monitored with a Meccomatic recording differential refractometer. Development is carried out until 150 fractions, 20 ml. each, are collected. Every other fraction from 72 through 150 is assayed at a dilution of 1:50. The bio-active peak in fractions 76 through 148 with a maximum in fractions 92 through 102 is observed. Fractions 86 through 113 are combined to give 580 ml. of solution which contains 71% of the bio-activity applied to the Dowex 50 × 8 column. This solution is then freeze-dried.

The freeze-dried solids obtained are dissolved in 0.1M 2,6-lutidine acetate pH 7.0 buffer to make 25 ml. This solution is applied to a bed of Bio-Gel P-2 (200–400 mesh) 5 × 108 cm., which had been previously equilibrated with 0.1M buffer. The gel is then developed with the same buffer at 9 ml./min. The effluent stream is monitored with a Mecco-matic recording differential refractometer. Development is continued until 105 fractions, 20 ml. each, are collected. Every fraction, 65 through 80, is assayed at a dilution of 1:200. The bio-active peak is observed in fractions 67 through 76. Fractions 70 through 72 are combined with and freeze-dried to yield 16.0 mg. with a potency of 13,800 units/mg. Fractions 69, 73 and 74 are combined and freeze-dried to yield 20.2 mg. with a potency of 5,200 units/mg.

The 16 mg. of freeze-dried solids is dissolved in 0.1M 2,6-lutidine acetate pH 7.0 buffer to make 10 ml. The solution is applied to a bed of Bio-Gel P-2, (200–400 mesh) 5 × 108 cm., which has been equilibrated with the same buffer. The gel is developed with buffer at 9 ml./min. The effluent stream is monitored with a Mecco-matic recording differential refractometer. Development is continued until 105 fractions of 20 ml. each has been collected. Every fraction, 65 through 80, is assayed at a dilution of 1:200.

The bio-active peak is observed in fractions 67 through 75. Fractions 68 through 72 are combined and freeze-dried to yield 9.1 mg. having a potency of 15,000 units/mg.

EXAMPLE 6

A tube of lyophilized culture of *Streptomyces cattleya* is opened aseptically and the contents suspended in 50 ml. of sterile Medium A contained in a 250 ml. baffled Erlenmeyer flask. Medium A has the following composition:

| Medium A | | |
|---|---|---|
| Yeast Autolysate (Ardamine*) | 10.0 | g |
| Glucose | 10.0 | g |
| Phosphate Buffer** | 2.0 | ml |
| $MgSO_4.7H_2O$ | 0.05 | g |
| Distilled $H_2O$ | 1000 | ml |
| pH: adjust to 6.5 using NaOH | | |
| *Ardamine: Yeast Products Corporation | | |
| **Phosphate Buffer Solution | | |
| $KH_2PO_4$ | 91.0 | g |
| $Na_2HPO_4$ | 95.0 | g |
| Distilled $H_2O$ | 1000 | ml |

The inoculated flask is shaken at 28° C. on a 220 rpm (2 throw) for 48 hours. Forty ml. of the 48-hour broth is removed aseptically and mixed with 40 ml. of sterile 20% (v/v) glycerol/water. Two ml. quantities of the resulting mixture are pipetted into sterile 1 dram vials which are then frozen and stored in the vapor phase of a liquid nitrogen freezer.

Frozen vial contents are used to inoculate a 250 ml. baffled Erlenmeyer flask containing 50 ml. of Medium A. This seed flask is shaken at 28° C. on a 160 rpm shaker at 28° C. for 24 hours.

Ten ml. portions from this seed flask are used to inoculate 2 liter baffled Erlenmeyer flask containing 500 ml. of Medium A. These seed flasks are shaken on a 160 rpm shaker at 28° C. for 24 hours.

A one thousand ml. portion of the pooled contents of these seed flasks in used to inoculate a 756 liter stainless steel fermentor containing 467 liters of Medium A. This tank is operated at 28° C. using an agitation rate of 130 rpm and an airflow of 10 cu. ft. per minute for 24 hours. Polyglycol 2000 (Dow chemical Corp.) is used as required as a defoamer but not to exceed 0.1%. Measurements of pH and dextrose are made and are as follows:

| Age (Hours) | 0 | 12 | 24 |
|---|---|---|---|
| pH | 6.4 | 6.4 | 6.6 |
| Dextrose mg./ml. | 8.1 | 8.1 | 8.1 |

Four hundred fifty-three liters of this growth are used to inoculate a 5670 liter stainless steel fermentor containing 4082 liters of Medium E, wherein Medium E has the composition:

| Medium E | | |
|---|---|---|
| Cerelose | 25.0 | g |
| Corn Steep Liquor (wet basis) | 15.0 | g |
| Distiller's Solubles | 10.0 | g |
| Cottonseed Media (Pharmamedia) | 5.0 | g |
| $CoCl_2.6H_2O$ | 0.01 | g |
| $CaCO_3$ (after pH adjustment) | 3.0 | g |
| Polyglycol 2000 | 0.25% | |
| Tap water | 1000 | ml |
| pH: adjust to 7.3 using NaOH | | |

This tank is operated at 24° C. using an agitation rate of 70 rpm and an airflow of 54.3 cu. ft. per minute for 144 hours. Defoamer, polyglycol 2000, is added as required but does not exceed 0.1%. Assays are performed using the supernatent of centrifuged broth. The results are tabulated in the table below under the heading "Antibiotic Activity vs ATCC 6538P". Assays are also run by the disc-diffusion procedure using ⅜ inch filter-paper discs and 10 ml. assay plates and the results tabulated in the table below under the heading "Antibiotic Activity (10 ml. plates)". The 10 ml. assay plates are prepared as follows: An overnight growth of the assay organism, *Staphylococcus aureus* ATCC 6538P, in nutrient broth plus 0.2% yeast extract is diluted with nutrient broth plus 0.2% yeast extract to a suspension having 40% transmittance at a wavelength of 660 mµ. This suspension is added to Difco nutrient agar supplemented with 2.0 g./l. Difco yeast extract, at 47° to 48° C., to make a composition containing 33.2 ml. of the suspension per liter of agar. Ten ml. of this suspension are poured into petri plates of 85 mm. diameter, and the plates are chilled and held at 4° C. until used (5 day maximum).

| Age | pH | Dextrose mg./ml. | Antibiotic Activity vs ATCC 6538P (mm.) | Antibiotic Activity (10 ml. plates) (mm.) |
|---|---|---|---|---|
| 0 | 6.6 | 22.2 | | |
| 12 | 6.3 | 20.2 | | |
| 24 | 5.8 | 18.0 | | 0 |
| 36 | 6.0 | 13.2 | | 21.5 |
| 48 | 6.0 | 8.6 | | 21.5 |
| 60 | 5.7 | 6.4 | | 26.5 |
| 72 | 5.8 | 2.7 | | 25.5 |
| 84 | 6.2 | 0.3 | | 27.5 |
| 96 | 6.4 | 0.2 | | 36.0 |
| 108 | 6.4 | 0 | | 35.0 |
| 120 | 6.3 | | 41.5 | 37.0 |
| 132 | 5.8 | | | 37.5 |
| 144 | 5.9 | | 43.0 | 37.5 |

The 4,082 liters of fermentation broth is filtered using a 30 inch filter press and a filter aid admix to the extent of 4% w/v. A 12 g. amount of (ehtylenedinitrilo) tetraacetic acid, sodium salt is added to the filtrate. The filtrate is cooled to 6° C., adjusted to pH 4.5 ± 0.2 and maintained at 6° C. The cold filtrate is adsorbed on 480 l. of Dowex 50 × 4 Na⁺, 20–50 mesh at about 48 l./min. The adsorbate is washed with 480 l. of deionized water and then eluted with 2% aqueous pyridine at 24 l./min. and three fractions of 300 l., 520 l. and 240 l. are collected and assayed at pH 7.0. The assays indicate that the eluate fractions contain 4%, 16% and 6%, respectively of the bio-activity applied on the Dowex 50 × 4 Na⁺ column. Eluate fraction two is concentrated to 48 l. and adjusted to pH 7.

The 48 l. concentrate is adjusted to pH 7.3 and adsorbed on 76 l. of Dowex 1 × 2, 50 to 100 mesh, chloride cycle resin at 7.6 l./min. The resin is eluted with deionized water at the same rate. Four fractions are collected, two of 48 l., one of 70 l. and one of 48 l. The fractions are adjusted to pH 7 as collected. Assays indicate that 68% of the starting bioactivity is in the 70 l. fraction. This fraction is concentrated to 18 l. at pH 7.0 and filtered using a 0.45 micron Millipore Filter. The filtrate is tray freeze-dried to yield 99 grams of product having a potency of 310 units/mg.

Ten g. of the freeze-dried solids are taken up in 0.1M 2,6-lutidine acetate buffer, pH 6.3. The solution, 125 ml. readjusted to pH 6.3 with acetic acid, is applied to a column of Dowex 50 × 8 (200–400mesh) in the 2,6-lutidine cycle, 7.6 × 142 cm., which had previously been equilibrated with buffer, and developed with 0.1M buffer at 25 ml./min. A 3 l. fore-cut is collected followed by 200 fractions of 20 ml. each. Every fourth fraction 36 through 192 is assayed at a dilution of 1:200. The bioactivity is contained in fractions 56 through 192, reaching a maximum in fractions 92 through 96. Fractions 80 through 136 are combined and 590 ml. of deionized water added to give 1760 ml. The pooled, diluted, solution containing 62% of the starting bio-activity applied on the Dowex 50 × 8 column, is freeze-dried.

The freeze-dried solids are dissolved in 0.1M 2,6-lutidine acetate, pH 7.0 buffer. The solution, 27 ml., is applied to a column of Bio-Gel P-2 (200–400 mesh) 5 × 112 cm. which has previously been equilibrated with 0.1M buffer. The gel is then developed with the same buffer at 10 ml./min.

The effluent stream is monitored with a Mecco-matic recording differential refractometer. The development is continued until 105 fractions, 20 ml. each, are collected. Every fraction, 70 through 93, is assayed at a dilution of 1:300. The bio-activity is found in fractions 73 through 82, reaching a maximum in fractions 77 and 78. Fractions 75 through 80 are freeze-dried to obtain 90 mg. of antibiotic with an average potency of 10,000 units/mg.

The 90 mg. of freeze-dried solid is taken up into 4 ml. of 0.01M potassium phosphate buffer, pH 7. This solution, containing 596 hydroxylamine-extinguishable optical density units (this measure of the thienamycin content being described at the end of this Example) is applied on a 1.7 cm. diameter column packed with 90 ml. prewashed XAD-2 and equilibrated prior to use with 180 ml. of 0.01M potassium phosphate buffer, pH 7, at 5° C. The XAD-2 is washed prior to use successively with (1) 5 volumes of 1N NaOH followed by deionized $H_2O$ effluent is neutral; (2) 5 volumes 1N HCl followed by deionized $H_2O$ until the effluent is neutral; (3) 5 volumes each of methanol, acetone, 0.001M EDTA tetrasodium, and finally distilled $H_2O$. Vacuum is applied to all solvents before use.

After the sample is applied on the column it is followed by two, 2 ml. portions of the phosphate buffer. The column is developed at 5° C. with the buffer at a flow rate of 2 ml./min. Four ml. fractions of eluate are collected. Fractions obtained after 100 ml. of eluate has been collected and ending with 253 ml. are combined and concentrated on a rotary evaporator under vacuum and below 10° C. to a volume of 6 ml.

This solution containing 436 hydroxylamine-extinguishable optical density units is applied on a 1.7 cm. diameter column packed with 0 ml. XAD-2 prewashed as above and equilibrated at 5° C. with distilled water. The sample is followed by two, 2 ml. portions of distilled water. The column is developed with distilled water at the rate of 2 ml./min. four ml. fractions of eluate are collected. Fractions obtained after 100 ml. of eluate has been collected and ending with 151 ml. are pooled and concentrated on a rotary evaporator to a volume of 2.73 ml. and the solution lyophilized to yield 6.49 mg. of thienamycin. Fractions obtained between 152 ml. and 345 ml. are pooled and concentrated on a rotary evaporator to a volume of 3.34 ml. and lyophilized to yield 11.53 mg. of antibiotic. These fractions contain a total of 369 hydroxylamine-extinguishable optical density units. This represents a 3.1 fold purification over the material applied to the first XAD-2 column and yields a calculated potency of 31,000 units/mg. Spectrophotometric analysis of a sample of this product shows an $E_{1cm.}^{1\%}=253$ when measured in phosphate buffer, pH 7, at 297 nm.

Hydroxylamine-Extinguishable Absorbance

The proportion of absorbance measured at 297 nm which can be attributed to the antibiotic content in impure samples is determined by the selective extinction of this absorbance (with concommitant inactivation of antibiotic activity) upon reaction with dilute hydroxylamine.

Samples are prepared in 0.01M potassium phosphate buffer at pH 7.0 to have an initial $A_{297}$ between 0.05 and 2.0. Freshly prepared, neutral hydroxylamine ($NH_2OH \cdot HCl$ plus NaOH to a final pH of 7) is added to a final concentration of 10 mM., and reaction is allowed to progress at room temperature for at least 30 min. The resulting $A_{297}$ when substracted from the initial reading (after correction for dilution by added reagent) yields the hydroxylamine-extinguishable absorbance. Solutions of pure thienamycin show a hydroxylamine-extinguishable absorbance of 94.5%.

EXAMPLE 7

A ten g. portion of the 99 g. freeze-dried solids obtained by the Dowex 1 × 2 purification in Example 6 is taken up in 0.1M 2,6-lutidine acetate buffer, pH 6.3. The solution, 125 ml., readjusted to pH 6.3 with acetic acid, is applied to a 7.6 × 142 cm. column of Dowex 50 × 8 in the 2,6-lutidine cycle, which has previously been equilibrated wit buffer. The column is developed with 0.1M buffer at 35 ml./min. A 3.6 l. fore-cut is collected followed by 200 fractions of 20 ml. each. Every fourth fraction 6 through 194 is assayed at a dilution of 1:200. The bio-activity is contained in fractions 18 through 178, reaching a maximum in fractions 62 through 82. Fractions 42 through 102 are combined an 640 ml. of deionized water added to give 1920 ml. The pooled, diluted, solution containing 63% of the bio-activity applied on the Dowex 50 × 8 column, is freeze-dried.

The freeze-dried solids are dissolved in 0.1M 2,6-lutidine acetate, pH 7.0 buffer. The solution, 25 ml., is applied to a 5 × 112 cm. column of Bio-Gel P-2 (200–400 mesh), which had previously been equilibrated with 0.1M buffer. The gel is then developed with the same buffer at 10 ml./min.

The effluent stream is monitored with a Mecco-matic recording differential refractometer. The development is continued until 125 fractions, 20 ml. each, are collected. Every fraction, 70 through 89, is assayed at a dilution of 1:300. The bio-activity is found in fractions 72 through 81, reaching a maximum in fraction 77. Fractions 75 through 79 are freeze-dried to obtain 100.5 mg. of antibiotic with a potency of 8,320 units/mg.

The 100.5 mg. of freeze-dried solid is taken up into 4 ml. of 0.01M potassium phosphate buffer, pH 7. This solution, containing 692 hydroxylamine-extinguishable optical units is applied on 1.7 cm. diameter column packed with 90 ml. prewashed XAD-2 and equilibrated prior to use with 180 ml. of 0.01M potassium phoshate buffer, pH 7, at 5° C. The XAD-2 is washed prior to use successively with (1) 5 volumes of 1N NaOH followed by deionized $H_2O$ until effluent is neutral; (2) 5 volumes 1N HCl followed by deionized $H_2O$ until the effluent is neutral; (3) 5 volumes each of methanal, acetone, 0.001M EDTA tetrasodium, and finally distilled H₂O. Vacuum to all solvents before use.

After the sample is applied on the column it is followed by two, 2 ml. portions of the phosphate buffer. The column is developed at 5° C. with the buffer at a flow rate of 2 ml./min. Four ml. fractions of eluate are collected. Fractions obtained after 109 ml. of eluate has been collected and ending with the 309th ml. are combined. To this combined eluate is added the 11.53 mg. sample of XAD-2 purified antibiotic obtained in Example 6 comprising 186 hydroxylamine-extinguishable optical density units. The combined eluate together with the added antibiotic is concentrated in vacuo on a rotary evaporator at a temperature below 10° C. to a volume of 7 ml.

This solution, containing 720 hydroxylamine-extinguishable optical density units is applied on a 1.7 cm. diameter column packed with 90 ml. XAD-2 prewashed as above and equilibrated at 5° C. prior to use with distilled water. The sample is followed by two, 2 ml. portions of distilled water. The column is developed with distilled water at the rate of 2 ml./min. Four ml. fractions of eluate are collected. Fractions obtained after 109 ml. of eluate have been collected and ending with the 301st ml. are pooled and concentrated on a rotary evaporator to a volume of 10.3 ml. This solution, containing 589 hydroxylamine-extinguishable optical density units, is lyophilized to yield 23.6 mg. of antibiotic with a calculated potency of 30,140 units/mg.

The antibiotic thus prepared is a white, amorphous solid with a fibrous consistency, a sample of which on exposure in a glass capillary tube to temperatures elevated at a rate of 3° C per minute, underwent decomposition without the intervention of a liquid phase in the following stages: softening occurred at 130° to 140° C. with a contraction in volume of the solid continuing until 170° to 174° C. in which range the material yellowed; sintering and a progressive intensification of color to reddish-brown being observed in the range 180° to 200° C. and finally carbonisation and residual traces of solid being found at 205° C.

A further sample of this material on spectrophotometric analyis shows an absorbance peak at 296.5 nm with an $E_{1cm}^{1\%} = 268.2$. Elemental analysis yields the following results: (1) a 5.67% weight loss upon drying at room temperature for 4 hours under vacuum, and (2) the composition 47.68% carbon, 6.22% hydrogen, 11.48% nitrogen. These results are consistent with the empirical formula $C_{11}H_{16}N_2O_4S \cdot (NH_3)_{0.28}$, the calculated elemental composition corresponding to this empirical formula being C=47.68%; H=6.13%, N=11.52%, S=11.57% and O=23.1%. Polarimetric analysis of a 1 mg./ml. solution of this sample in 10 mM potassium phosphate buffer showed a specific optical rotation $[\alpha]_D^{27° C.} + 80$. The infrared spectrum (FIG. 1) of a nujor mull of this sample revealed characteristic absorption peaks at 1765 cm.⁻¹, 1650–1550 cm.⁻¹, 2800–2500 cm.⁻¹, and 3500–3100 cm.⁻¹. An NMR spectrum at 100 MHz of a sample of this product dissolved in D₂O revealed a doublet at δ1.275, a pair of doublets at δ3.39 and multiplets at δ3.15 and δ4.20, these peaks being characteristic of thienamycin.

Any departure from the above description for the isolation and purification of thienamycin which conforms to the present invention is intended to be included within the scope of the claims.

What is claimed is:

1. A process for recovering the antibiotic thienamycin from fermentation broths or from solutions containing said antibiotic which comprises passing a fermentation broth or a solution containing said antibiotic through a column packed with a cation exchange resin containing sulfonic acid exchange groups; eluting the resin adsorbate with a base; collecting the eluates; combining the active fractions; and passing said combined fractions through a column packed with polyacrylamide or dextran gel which excludes molecules having a molecular weight greater than 1,800 and 700 respectively; eluting the gel with water or with an aqueous solution of a lower alcohol; collecting the eluates and combining the active fractions.

2. A process for recovering the antibiotic thienamycin from fermentation broths or from solutions containing said antibiotic which comprises passing a fermentation broth or a solution containing said antibiotic through a column packed with a cation exchange resin containing sulfonic acid exchange groups; eluting the resin adsorbate with a base; collecting the eluates; combining the active fractions; percolating said active fractions eluted from the cation exchange resin through a column packed with an anion exchange resin of the polystryrene-quaternary ammonium type; collecting the effluent; passing the effluent through a column packed with polyacrylamide or dextran gel which excludes molecules having a molecular weight greater than 1,800 and 700 respectively; eluting the gel with water or with an aqueous solution of a lower alcohol; collecting the eluates and combining the active fractions.

3. A process for recovering the antibiotic thienamycin from fermentation broths or from solutions containing said antibiotic which comprises passing a fermentation broth or a solution containing said antibiotic through a column packed with a cation exchange resin containing sulfonic acid exchange groups; eluting the resin adsorbate with a base; collecting the eluates; combining the active fractions; percolating said active fractions eluted from the cation exchange resin throgh a column packed with an anion exchange resin of the polystyrene-quarternary ammonium type; collecting the effluent; passing said effluent through a column packed with a cation exchange resin containing nuclear sulfonic acid exchange groups; eluting the resin adsorbate with a buffer or water; combining the active fractions; passing said active fractions through a column packed with polyacrylamide or dextran gel which excludes molecules having a molecular weight greater than 1,800 and 700 respectively; eluting the gel with water or with an aqueous solution of a lower alcohol; collecting the eluates; combining the active fractions; concentrating said fractions; adsorbing said concentrate on a column packed with a polystyrene, hydrophobic cross-linked divinylbenzene polymer; eluting the polymer with water; collecting the eluate and combining the active fractions.

4. A process for recovering the antibiotic thienamycin from fermentation broths or from solutions containing said antibiotic which comprises passing a fermentation broth or a solution containing said antibiotic through a column packed with a cation exchange resin containing sulfonic acid exchange groups; eluting the resin adsorbate with a base; collecting the eluates; combining the active fractions; percolating said active fractions eluted from the cation exchange resin through a column packed with an anion exchange resin of the polystyrene-quaternary ammonium type; concentrating the effluent; adsorbing the concentrated effluent on a column packed with a polystyrene, hydrophobic crosslinked divinylbenzene polymer; eluting the polymer with water; collecting the eluate and combining the active fractions.

5. The process of claim 4 which comprises eluting the polystyrene, hydrophobic crosslinked divinylbenzene polymer with phosphate buffer; collecting the eluate; combining the active fractions; adsorbing the active fractions on a column packed with a polystyrene, hydrophobic crosslinked divinylbenzene polymer; eluting the polymer with water; collecting the eluate and combining the active fractions.

6. A process for recovering the antibiotic thienamycin free of inorganic ions which comprises adsorbing solutions containing thienamycin and inorganic ions on a column packed with the polystyrene resin, XAD-2; eluting the polymer with water; collecting the eluate and combining the active fractions.

7. The process according to claim 3 which additionally comprises passing said active fractions eluted from polyacrylamide or dextran gel at least once through a column packed with a poly-styrene, hydrophobic crosslinked divinyl benzene polymer, eluting with phosphate buffer or water; collecting the eluates and combining the active fractions.

8. The process of claim 1 wherein the cation exchange resin is composed of sulfonic exchange groups in the sodium cycle attached to a styrene-divinylbenzene matrix.

9. The process of claim 2 wherein the cation exchange resin is composed of sulfonic exchange groups in the sodium cycle attached to a styrene-divinylbenzene matrix.

10. The process of claim 3 wherein the cation exchange resin is composed of sulfonic groups in the sodium cycle attached to a styrene-divinylbenzene matrix.

11. The process of claim 2 wherein the anion exchange resin is composed of quaternary ammonium exchange groups in the chloride cycle attached to a styrene-divinylbenzene polymer matrix.

12. The process of claim 1 wherein the polyacrylamide gel is eluted with n-butanol:water (1:99).

13. The process of claim 1 wherein the column packed with the cation exchange resin is eluted with an aqueous solution of an organic base wherein the base is selected from the group consisting of pyridine; $\alpha,\beta,\gamma$-picoline; 2,3-;2,4-; and 2,6-lutidine; 2,4,6-collidine and alkylamines wherein the alkyl groups contain 2 to 10 carbon atoms.

14. The process of claim 3 wherein said buffer is selected from the group consisting of tris(hydroxymethyl)aminomethane maleate, cacodylic acid, $KH_2PO_4$, $NaH_2PO_4$, N-ethylmorpholine, $\alpha$-, $\beta$- or $\gamma$-picoline and 2,3-;2,4-; and 2,6-lutidine.

15. The process according to claim 7 wherein the columns packed with the polystyrene, hydrophobic crosslinked divinyl benzene polymer are eluted with phosphate buffer at neutral pH.

* * * * *